(12) United States Patent
Kubo et al.

(10) Patent No.: US 6,602,200 B1
(45) Date of Patent: Aug. 5, 2003

(54) ELECTRONIC BLOOD PRESSURE METER

(75) Inventors: Takeshi Kubo, Kyoto (JP); Masashi Fukura, Kyoto (JP); Akira Nakagawa, Kyoto (JP); Yoshinori Miyawaki, Kyoto (JP)

(73) Assignee: Omron Corporation, Kyoto (JP)

( * ) Notice: Subject to any disclaimer, the term of this patent is extended or adjusted under 35 U.S.C. 154(b) by 35 days.

(21) Appl. No.: 09/830,859

(22) PCT Filed: Sep. 7, 2000

(86) PCT No.: PCT/JP00/06113

§ 371 (c)(1),
(2), (4) Date: May 2, 2001

(87) PCT Pub. No.: WO01/17427

PCT Pub. Date: Mar. 15, 2001

(30) Foreign Application Priority Data

Sep. 8, 1999 (JP) .......................................... 11-253808

(51) Int. Cl.$^7$ ................................................. A61B 5/02
(52) U.S. Cl. ....................................... 600/494; 600/485
(58) Field of Search ................................ 600/450, 454, 600/481, 526, 527, 561, 482, 483, 484, 485–507

(56) References Cited

U.S. PATENT DOCUMENTS

| 4,625,277 A | 11/1986 | Pearce et al. |
| 5,052,397 A | 10/1991 | Ramsey, III et al. |
| 5,743,857 A | * 4/1998 | Shinoda et al. ............. 600/492 |
| 5,865,756 A | 2/1999 | Peel, III |
| 5,913,826 A | * 6/1999 | Blank ......................... 600/500 |
| 6,168,567 B1 | * 1/2001 | Pickering et al. ........... 600/490 |

FOREIGN PATENT DOCUMENTS

| JP | 58-188428 | 11/1983 |
| JP | 60-40038 | 3/1985 |
| JP | 61-206427 | 9/1986 |
| JP | 63-97145 | 4/1988 |
| JP | 1-256930 | 10/1989 |
| JP | 4-152933 | 5/1992 |
| JP | 4-259449 | 9/1992 |
| JP | 5-31082 | 2/1993 |
| JP | 5-84221 | 4/1993 |
| JP | 5-168601 | 7/1993 |
| JP | 5-200005 | 8/1993 |
| JP | 5-337090 | 12/1993 |

* cited by examiner

*Primary Examiner*—Mahmoud Gimie
(74) *Attorney, Agent, or Firm*—Morrison & Foerster LLP (57) ABSTRACT

An electronic blood pressure meter determines, in an inflation process, pressure Ps correlated to systolic pressure, pressure Pd correlated to diastolic pressure and pulse wave period Pc, and then calculates deflation rate def–v in a deflation process based on a first formula (def–v=(Ps–Pd–mb1)×Pc/N, where N represents the number of required beats). Further, maximum inflation value Inf–max is calculated based on a second formula (Inf–max=def–v·(np×Pc+α)+Ps+β1). The pressure is increased to reach the calculated maximum value and then deflation is started at the calculated deflation rate. The blood pressure meter can thus perform a precise measurement in a shortest time.

10 Claims, 8 Drawing Sheets

ELECTRONIC BLOOD PRESSURE METER

FIELD OF THE INVENTION

The present invention relates to an electronic blood pressure meter.

DESCRIPTION OF THE RELATED ART

An electronic blood pressure meter generally determines systolic and diastolic pressures by first inflating a cuff to pressurize an artery of a human body and then using information on the blood vessel such as pulse wave and K-sounds as well as cuff pressure in a subsequent deflation process.

There have conventionally been some deflation methods namely deflation methods as discussed below, employed in this type of electronic blood pressure meter in measurement.

1. Displacement adjusting means is controlled to allow pressure to decrease at a constant rate which is set in advance.
2. Displacement adjusting means is controlled to allow pressure to decrease at a rate calculated according to a detected pressure in a cuff and pulse (Japanese Patent Laying-Open Nos. 5-84221 and 5-337090).
3. Deflation rate is adjusted according to irregularities in the amplitude of pulse wave in inflation (Japanese Patent Laying-Open No. 5-200005).

A conventional electronic blood pressure meter has a system of automatically setting of inflate pressure by estimating from pulse wave observed in inflation a systolic pressure or any relevant value and adding a constant pressure to the estimated systolic pressure to use the resultant value for setting inflation.

A conventional electronic blood pressure meter employs a system of controlling a deflation rate. This system implements a high speed control by changing a voltage applied to a control valve at short periods to enable the deflation rate to speedily reach a target rate after inflation is completed and then using normal control periods when the deflation rate attains the target rate in order to calculate blood pressure.

One of those systems of deflation employed in conventional electronic blood pressure meters, the first system implements a constant deflation rate. If a subject has a low pulse or a low pulse pressure, the number of pulse waves detected during displacement between the systolic and diastolic pressures is small, and accordingly an accurate measurement of blood pressure is impossible. When the displacement rate is decreased for detecting a sufficient number of pulse waves, a longer time is required for measurement, resulting in a greater load on the subject due to congestion and long-term inflation.

According to the second system, the deflation rate is independent of pulse pressure. Then, the number of pulse waves of a subject having a low pulse pressure is small, which deteriorates measurement precision.

On the other hand, a subject having hypertension and a high pulse pressure feels uncomfortable and pain, because of inflation by a cuff for an excessively long period of time.

The third system has a problem that the deflation rate cannot be increased when a subject has a normal pulse.

The automatic inflation setting system of the conventional electronic blood pressure meter discussed above always adds a fixed value to a systolic pressure. Therefore, particularly a subject having a relatively fast pulse is excessively pressurized in measurement, feeling uncomfortable and pain.

In order to set the deflation rate higher than a conventional rate, a fixed value (inflation margin) to be added must be large since it is necessary to detect at least one pulsation at a pressure higher than the systolic pressure in deflation.

The system of controlling deflation rate employed in the conventional electronic blood pressure meter sets a high initial value as a control valve drive voltage that is enough to close the valve. Therefore, even if a high-rate control is conducted, there occurs a delay of a few seconds before a drive voltage is reached that enables the target deflation rate. Resultant problems are that measurement takes a longer time and that measurement cannot be started until pressure is applied to a human body more than necessary.

The present invention has been made to overcome the problems above. One object of the invention is to provide an electronic blood pressure meter capable of taking measurements as fast as possible without deteriorating precision.

SUMMARY OF THE INVENTION

An electronic blood pressure meter according to the present invention determines blood pressure in a process of gradually depressurizing an artery of at least one area of a human body that has been pressurized to a level higher than systolic pressure. The electronic blood pressure meter includes pulse wave detecting means for detecting oscillation of a blood vessel wall or pulsating blood flow in the artery occurring in the inflation process, pulse wave period measuring means calculating, when the pulse wave detecting means detects a plurality of pulse waves, a period between occurrences of respective pulsations, pulse wave feature amount calculating means receiving as inputs a pulse wave signal of one or a plurality of pulsations supplied from the pulse wave detecting means and a representative pressure value synchronizing with pulse wave generation timing supplied from pressure detecting means for detecting pressure at the pressurized area of the human body, for extracting a feature amount correlated to at least two of systolic pressure, diastolic pressure and mean blood pressure or correlated to systolic pressure only, and deflation rate calculating means according to an output from the pulse wave feature amount calculating means and the pulse wave period measured by the pulse wave period measuring means for calculating a target deflation rate. The deflation rate calculating means uses the feature amount calculated by the pulse wave feature amount calculating means to calculate and determine the target deflation rate to enable detection of a predetermined number of pulse waves between systolic pressure and diastolic pressure in measurement performed in the deflation process.

An optimum deflation rate is thus determined and accordingly pulse waves that can be detected in deflation are minimum in number while the number satisfies a number necessary for assuring precision.

Preferably, the electronic blood pressure meter further includes target inflation value setting means for determining a target inflation value according to an output from the pulse wave feature amount calculating means.

An optimum and minimum target inflation value is thus determined and accordingly only a minimum pressure that is necessary is applied to avoid excessive inflation by extra pressure.

Further, an electronic blood pressure meter according to the invention determines blood pressure in a process of gradually depressurizing an artery of at least one area of a human body that has been pressurized to a level higher than systolic pressure, and includes fluid pressure control means for controlling deflation rate by adjusting flow rate of fluid. The electronic blood pressure meter further includes means for detecting information on change of inflation force in the inflation process, and initial rate-control-value determining means using the pressure change information for indicating an initial value of a feature amount at start of deflation to the fluid pressure control means. Based on the pressure rising state in the inflation process, pressure pump drive voltage, pressure at start of deflation and voltage-flow rate characteristics of a control valve, a voltage is applied as an initial value to drive the control valve such that a flow rate is accomplished to immediately reach a target rate. Then, immediately after inflation is completed, deflation is stably controlled at a target deflation rate. There is no wasteful time nor extra inflation before control becomes stable, and thus the time and pressure are minimum that are required while precision is assured.

DETAILED DESCRIPTION OF THE INVENTION

Figure 1:
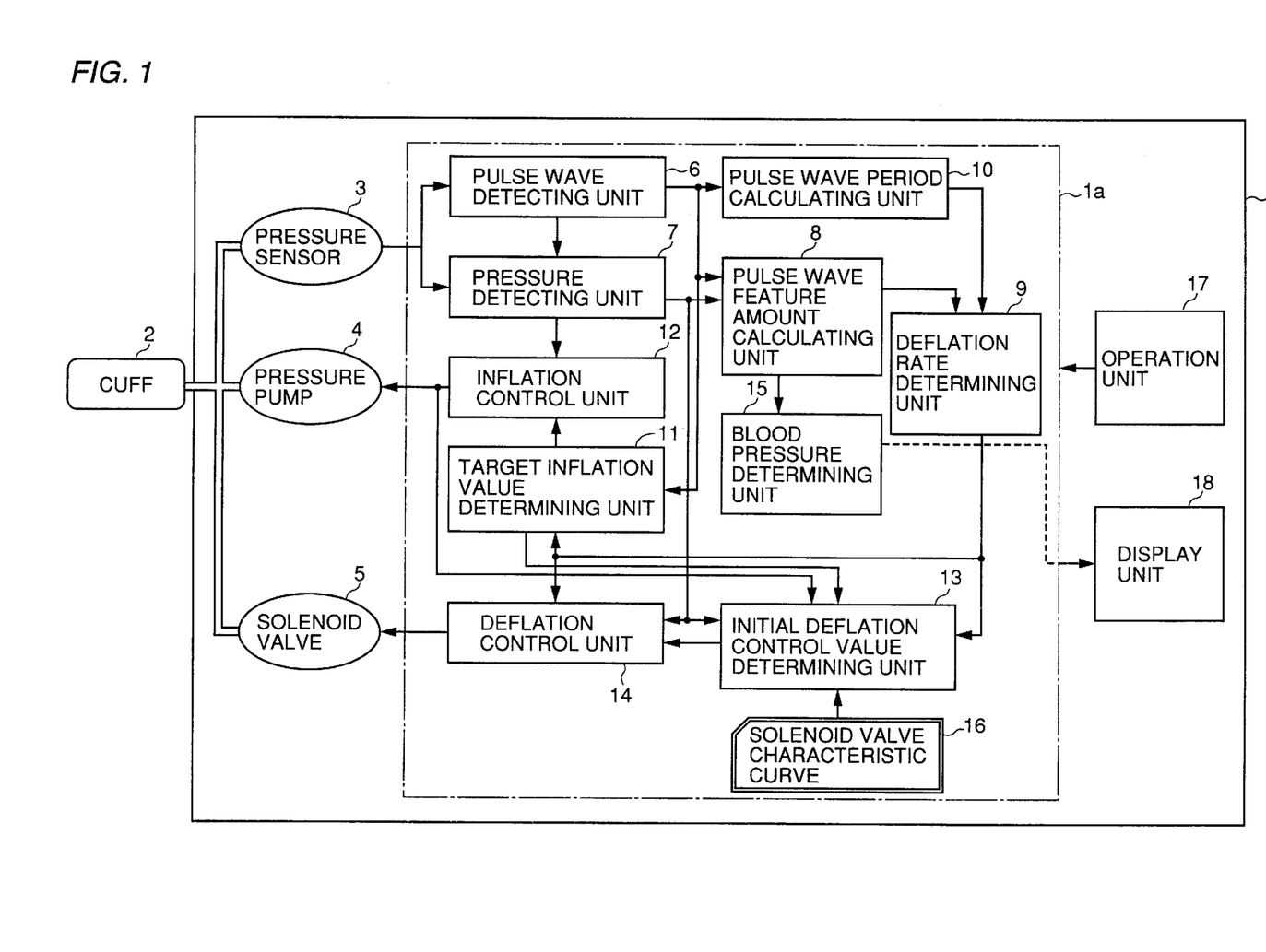
FIG. 1 is a block diagram showing a circuit structure of an electronic blood pressure meter as one embodiment of the invention.

The present invention is hereinafter described in more detail in conjunction with an embodiment. FIG. 1 is a block diagram of an electronic blood pressure meter of one embodiment of the invention. The electronic blood pressure meter is structured of a body 1 of the blood pressure meter and a cuff 2 affixed to a measurement site of a human body. Blood pressure meter body 1 includes a pressure sensor 3 detecting a cuff pressure, a pressure pump 4 pressurizing the cuff, a solenoid valve 5 adjusting a flow rate at which air within the cuff is released to the outside to accomplish deflation, operational control units discussed below structured within a one-chip microcomputer 1a, an operation unit 17 for turning on/off power, starting measurement and the like, and a display unit 18 indicating measurements such as blood pressure value and pulse.

One-chip microcomputer 1a includes a pulse wave detecting unit 6 detecting a pulse wave signal superimposed on a pressure signal output from pressure sensor 3, a pressure detecting unit 7 converting the pressure signal into a pressure value, outputting the pressure value and detecting a representative pressure value of the cuff when a pulse wave occurs, a pulse wave feature amount calculating unit 8 extracting a future amount from the pulse wave signal and the representative pressure value, and using the extracted feature amount together with the representative pressure value to determine a parameter correlated with a blood pressure value, a deflation rate determining unit 9 determining a deflation rate from the parameter correlated to the blood pressure value, a pulse wave period calculating unit 10 calculating the period of the detected pulse wave signal, a target inflation value determining unit 11 determining a inflation setting value from the parameter correlated to the blood pressure value, a inflation control unit 12 controlling a drive voltage for pressure pump 4, an initial rate control value determining unit 13 determining an initial value of a solenoid valve drive voltage at the start of deflation, a deflation control unit 14 controlling the drive voltage for solenoid valve 5 to accomplish deflation at the target deflation rate determined by deflation rate determining unit 9, a blood pressure calculating unit 15 determining a blood pressure from an output of the pulse wave feature amount calculating unit, and a solenoid valve characteristic curve 16 that is data on (drive voltage)-(flow rate) characteristics stored in advance in a ROM or the like.

Figure 2:
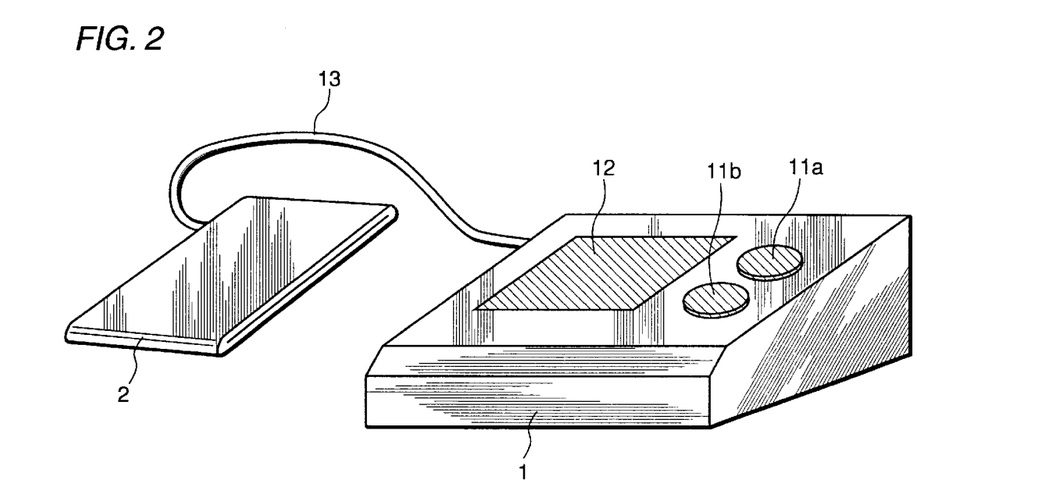
FIG. 2 is a perspective external view of the electronic blood pressure meter of the embodiment.

FIG. 2 is a perspective external view of the electronic blood pressure meter of this embodiment. Blood pressure meter body 1 has a power switch 11a and a measurement start switch 11b in addition to display unit 12 on the top surface.

Figure 3:
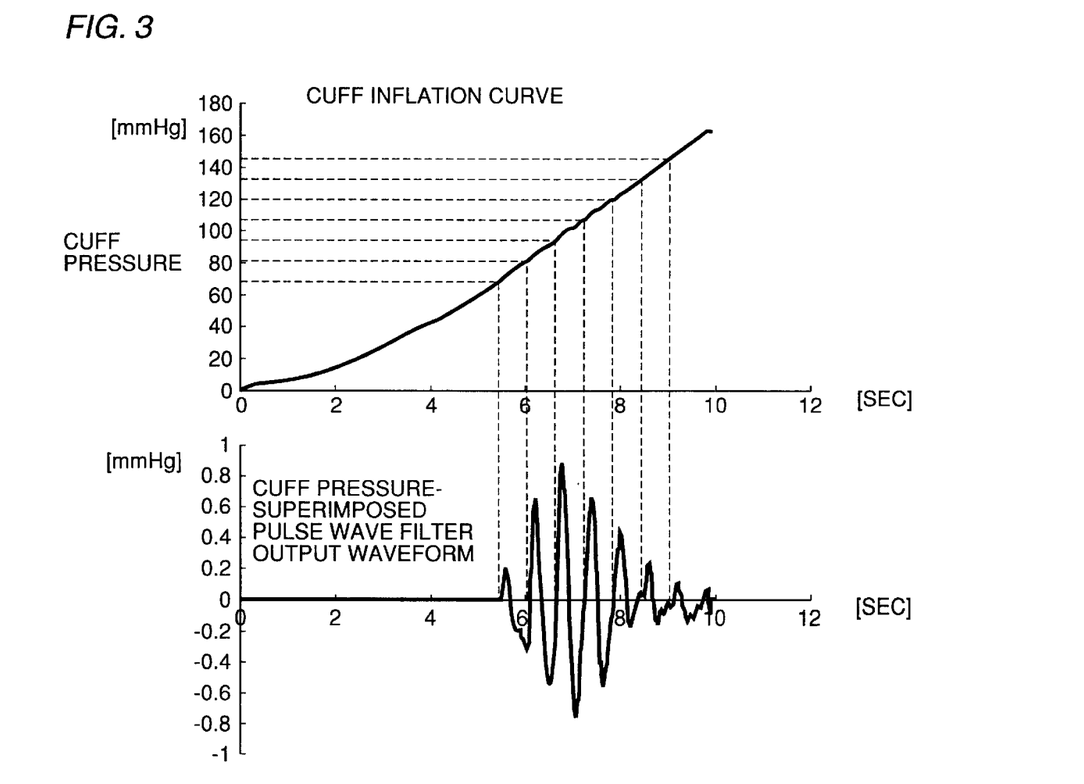
FIG. 3 shows cuff pressure extracted by the electronic blood pressure meter of the embodiment that changes with time.

Operations of respective components of the electronic blood pressure meter of this embodiment are described below. Measurement of blood pressure is started in a resting state by wrapping cuff 2 around a measurement site. With power switch 11a turned on, measurement start switch 11b is pressed to start measurement. Then, air is supplied into cuff 2 by pressure pump unit 4 to raise the pressure in the cuff. The cuff pressure is converted into a pressure signal by pressure sensor 3 and means such as AD conversion is used to enable one-chip microcomputer 1a to take the signal as a pressure signal. Pulse wave detecting unit 6 derives a pulse wave signal superimposed on the pressure signal. The pressure signal when pressure is applied and the extracted pulse wave signal are shown in FIG. 3.

Pressure detecting unit 7 makes corrections to the pressure signal, specifically, linearity correction and drift correction in terms of environmental change such as temperature for pressure sensor 3, and then outputs a correct pressure value. Further, pressure detecting unit 7 outputs a representative pressure value when the pulse wave occurs in synchronization with a pulse wave detection timing signal supplied from pulse wave detecting unit 6. A relation between the pulse wave signal and the representative pressure value is shown in FIG. 3.

Figure 4A:
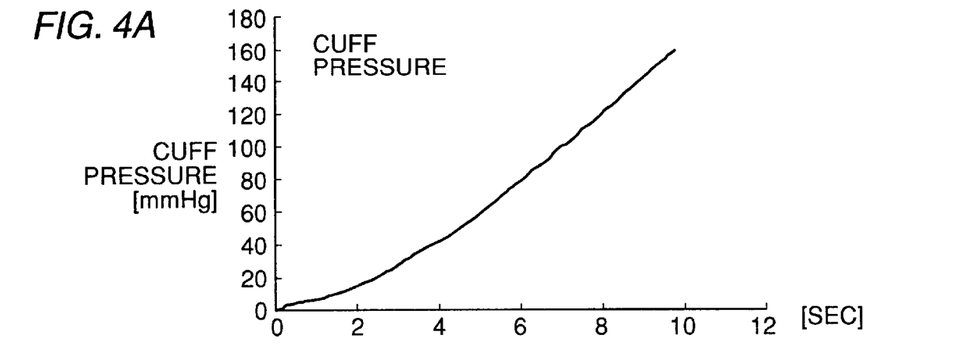
FIGS. 4A–4C illustrate cuff pressure changing with time, pulse wave amplitude, and representative pressure with respect to the pulse wave.
Figure 4B:
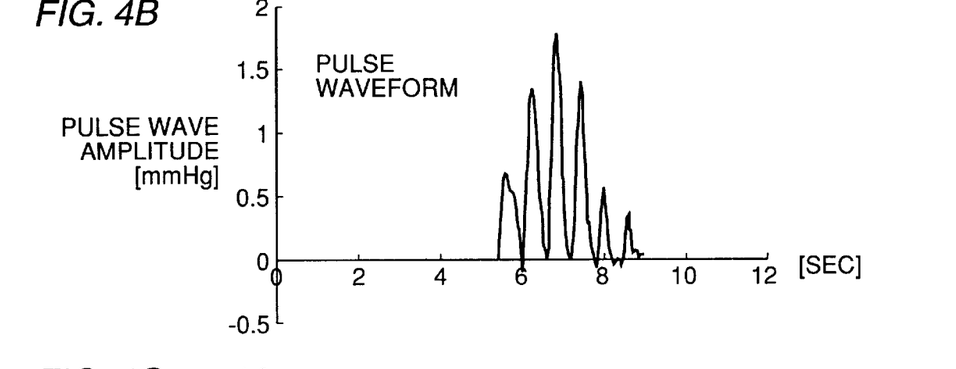
Figure 4C:
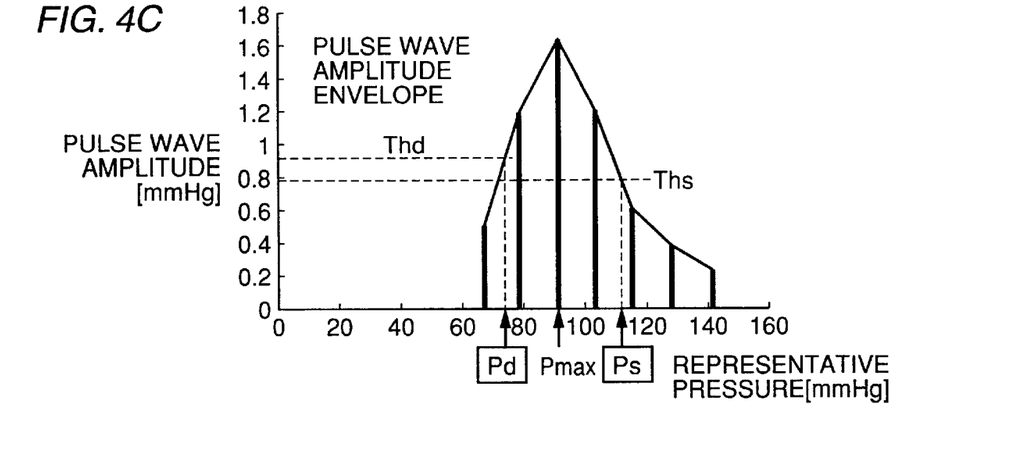

Pulse wave feature amount calculating unit 8 calculates a pulse wave feature amount correlated with blood pressure from the pulse wave signal output from pulse wave detecting unit 6 and the representative pressure value output from pressure detecting unit 7, and outputs a resultant value. An exemplary calculation of the pulse wave feature amount is described below. There are a large number of features of a pulse waveform that change according to the relation between human blood pressure value and cuff pressure, such as pulse wave amplitude, pulse wave area, and pulse wave width (time period where the pulse wave amplitude is greater than a certain threshold). Here, the pulse wave amplitude and the pulse wave width are described. FIGS. 4A–4C respectively show cuff pressure in inflation (FIG. 4A), pulse waveform extracted from the cuff pressure signal (FIG. 4B), and a graph having its horizontal axis indicating cuff pressure at the time of occurrence of a pulse wave as a representative pressure value and vertical axis indicating pulse wave amplitude at that time (FIG. 4C). The pulse wave amplitude represents a commonly well-known method as a method of measuring blood pressure by oscillometry. The amplitude is maximum near the point at which the cuff pressure is equal to a mean blood pressure. The amplitude sharply decreases in the regions where pressure is lower than the diastolic pressure and higher than the systolic pressure.

FIG. 4C shows pressure Pmax at the maximum amplitude, pressures Ps and Pd where a pulse wave amplitude envelop crosses constant thresholds Ths and Thd respectively. Here, Ps, Pd and Pmax are closely correlated to systolic, diastolic and mean pressures respectively.

Figure 5:
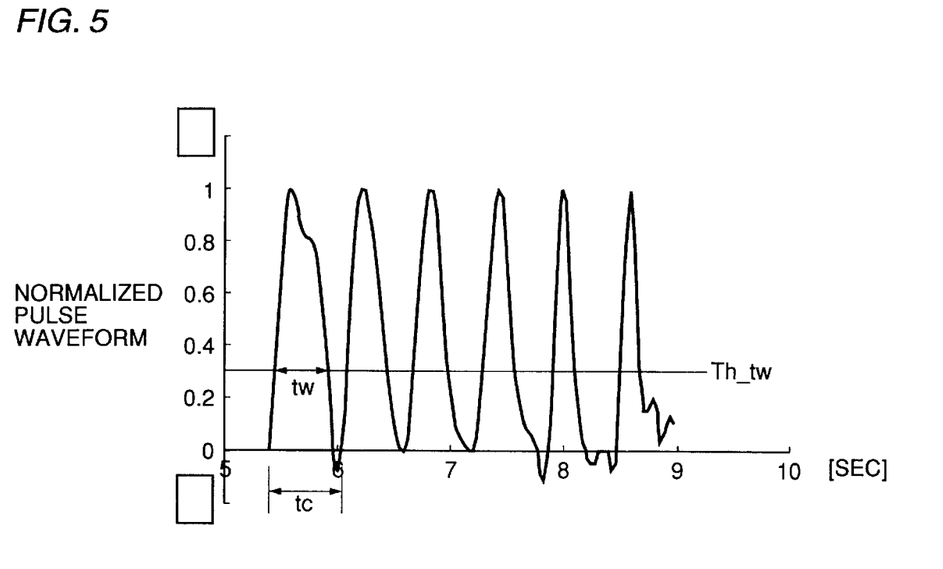
FIG. 5 shows a pulse waveform with a normalized amplitude.
Figure 6:
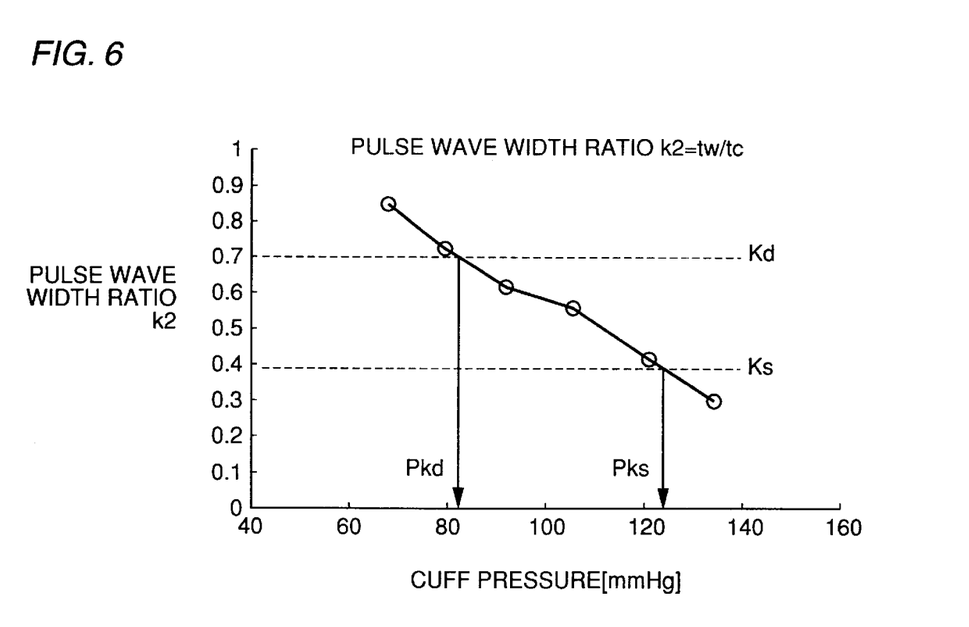
FIG. 6 shows a relation between cuff pressure and pulse wave width ratio.

FIG. 5 shows a normalized pulse waveform produced by normalizing the maximum amplitude of the pulse wave itself such that all pulse waveforms as described in conjunction with FIGS. 4A–4C have the same amplitude. Further, in order to normalize difference of pulse wave width between individuals, pulse wave width tw is divided by pulse wave period tc and its result K2 is shown in FIG. 6. The pulse wave width rate K2 is high near the diastolic pressure and decreases as the systolic pressure is approached. Therefore, pressures Pks and Pkd at which pulse wave width rate K2 is equal to constant thresholds Ks and Kd have values well correlated to systolic and diastolic pressures.

A method of deciding deflation rate by using feature amounts Ps, Pd, Pmax or Pks and Pkd correlated to blood pressure as described above is described below. Deflation rate determining unit 9 determines deflation rate by means of following formulas using as inputs feature amounts Ps, Pd, Pmax or Pks and Pkd supplied from pulse wave feature amount calculating unit 8.

1) Ps and Pd are used.

$$\text{deflation rate: } def\text{-}v = (Ps - Pd - mb1) \times Pc/N \quad (1)$$

2) Ps and Pmax are used.

$$\text{deflation rate: } def\text{-}v = (3 \cdot Ps - 3 \cdot Pmax - mb2) \times Pc/N \quad (2)$$

3) Pd and Pmax are used.

$$\text{deflation rate: } def\text{-}v = (3/2 \cdot Pmax - 3/2 \cdot Pd - mb3) \times PC/N \quad (3)$$

4) Ps is used.

$$\text{deflation rate: } def\text{-}v = (a \cdot Ps + b - mb4) \times Pc/N \quad (4)$$

Here, Pc represents pulse period calculated by pulse period calculating unit 10. If Pc is not used, a fixed value, i.e., period Pc=1 second, may be used that is calculated from a normal number of beats, 60 beats/min, for example.

N represents the number of beats occurring between the systolic and diastolic pressures in deflation, namely in pulse pressure. It is confirmed through experiments and is also clearly understood from measurement principles that an increased N lowers the deflation rate and increases the number of beats occurring in pulse pressure while a decreased N reduces the number of beats and N in the range of 2–3 enormously deteriorates measurement precision. Accordingly, the value of N should be set in consideration of the performance of deflation measurement algorithm. Usually an appropriate value of N is approximately 5.

The operations in parentheses of formulas (1)–(4) above are all performed for determining pulse pressure (systolic pressure—diastolic pressure). Values of mb1–mb4 are respectively determined in consideration of offset amount in pulse pressure calculation and for avoiding too high deflation rate. Actual values are set in advance by adjusting them in accordance with values of Ths and Thd that are thresholds for calculating the parameters discussed above.

When Ths and Thd are adjusted such that pressure values Ps and Pd agree best to systolic and diastolic pressures, there is presented an example of determining deflation rate by using at least two of systolic pressure, mean blood pressure and diastolic pressure or using only systolic pressure.

The deflation rate is determined by using feature amounts Pks and Pkd as inputs that are calculated from pulse wave width ratio, as shown by the following formula.

$$\text{deflation rate: } def\text{-}v = (Pks - Pkd - mb5) \times Pc/N \quad (5)$$

Pc represents the pulse period and N represents the number of beats detected in pulse pressure as described above. Mb5 is also set in advance by adjusting it in accordance with offset amount for calculating pulse pressure and values of Ks and Kd used for calculating parameters Pks and Pkd.

As described above, the deflation rate is determined according to information on pulse wave in the inflation process and then the target inflation value is set. When the pressure in the cuff reaches the target value, inflation is stopped to enter the deflation process for measurement. The target inflation value is set such that at least one pulsation is detected at a pressure higher than the systolic pressure in transition to the deflation process. Another method is possible by means of extrapolation or the like to estimate pulse wave at a pressure without inflation actually. In this case, inflation to any value near systolic pressure is necessary in actual for keeping measurement precision.

The target inflation value is determined according to a feature amount in inflation that is correlated to a systolic pressure to be measured, or based on a systolic pressure estimated in inflation. The time period from the transition to the deflation measurement to the first detection of a pulse which is valid in measurement changes depending on the pulse rate of a subject to be measured and depending on the timing of transition to the deflation. For example, if a subject to be measured has a pulse rate of 60 beats/min and the deflation rate is 10 mmHg/sec, the first value is detected after the pressure decrease of maximum 10 mmHg. Therefore, when the pressure is reduced at such a high rate, the pressure cannot be measured properly unless the target inflation value is determined in consideration of the deflation rate.

The electronic blood pressure meter according to this embodiment has a device that uses the feature amount correlated to the systolic pressure and the deflation rate thereby sets the target inflation value. Therefore, the electronic blood pressure meter can perform measurement with a minimum inflation.

Specifically, the target inflation value is determined by the following formulas in target inflation value determining unit 11 by using feature amounts Ps, Pd and Pmax output from pulse wave feature amount calculating unit 8 as described above.

1) target inflation value: $Inf\text{-}\max = def\text{-}v \cdot (np \times Pc + \alpha) + Ps + \beta 1$ (6)

2) target inflation value: $Inf\text{-}\max = def\text{-}v \cdot (np \times Pc + \alpha) + (3 \cdot Pmax - Pd) + \beta 2$ (7)

Where def–v represents deflation rate output from deflation rate determining unit 9, np is the number of beats detected at a pressure higher than the systolic pressure in the deflation process, and Pc represents pulse period. β1 and β2 are set such that terms Ps+β1 and (3·Pmax–Pd)+β2 in formulas (6) and (7) respectively are close to systolic pressure and β1 and β2 change depending on values of thresholds Ths and Thd for determining feature amounts.

Figure 7:
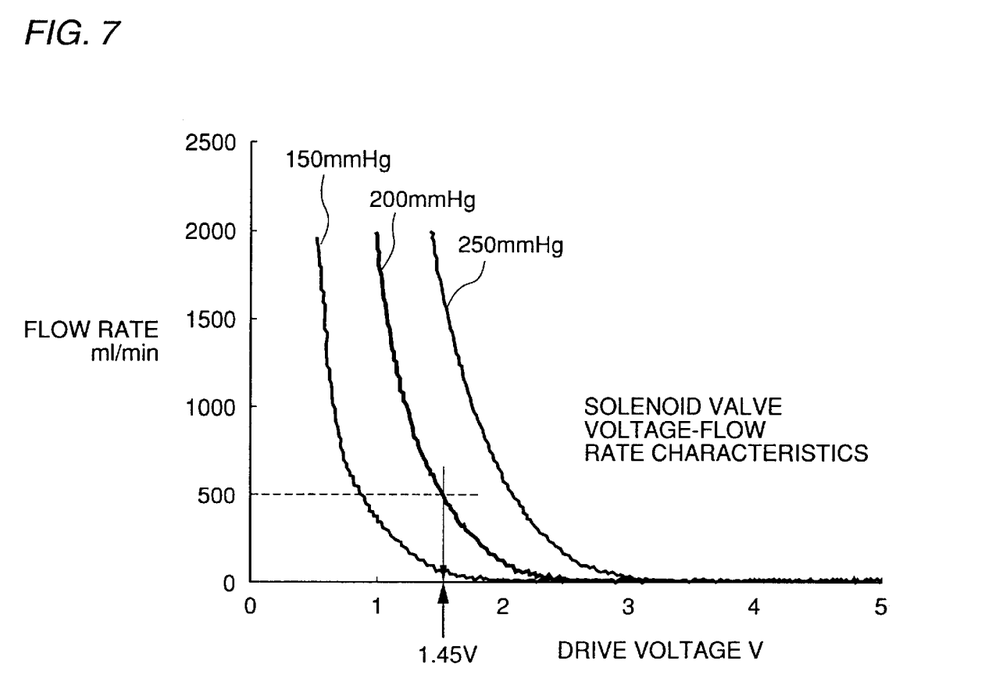
FIG. 7 shows voltage-flow rate characteristics of a solenoid valve of the electronic blood pressure meter shown in FIG. 1.

When the pressure in the cuff reaches the target inflation value, deflation is started at the set target rate to perform measurement in the deflation process. Solenoid valve 5 to be used should change flow rate according to drive voltage. FIG. 7 shows voltage-flow rate characteristics. When the deflation rate is controlled such that the rate is set to a target value, delay occurs in the period from the time when solenoid valve 5 is closed enough in inflation to the time when the voltage enables the flow rate to cause the target deflation rate. This means that the target inflation value must be set higher enough to absorb this delay. Consequently, an increased measurement time as well as a higher inflation value add load to a subject. In order to solve this problem, initial deflation rate determining means 13 is provided. Then, an initial value of the drive voltage for solenoid 5 can be set to a voltage which can provide a flow rate achieving a target rate. Accordingly, after inflation is completed, a target deflation rate is immediately reached. Initial deflation control value determining unit 13 determines an initial valve drive voltage as follows by using pressure P(i) output from pressure detecting unit 7, pump drive voltage Vb output from inflation control unit 12, pressure at the end of inflation Inf–max, and voltage-flow rate characteristic curve of the solenoid valve.

First, compliance Cp when the inflation is ended is determined by the following formula.

$$Cp=\{P(i)31\ P(i-1)\}/Vb \quad (8)$$

In formula (8), Vb represents pressure pump drive voltage, that is proportional to pumping amount. P(i)–P(i–1) represents an amount of change per one sampling of pressure value, and compliance Cp is an amount of change of cuff pressure, i.e., ratio between inflation rate and flow rate for inflating the cuff. i represents the number of samplings and P(i) means a sampling pressure value for the i-th sampling. When pressure is sampled i times before inflation is completed, the pressure value at the end of inflation (i–st sampling) is indicated by P(i), the pressure value of (i–1)-th sampling preceding the final sampling by one is indicated by P(i–1), and the difference therebetween is divided by pump voltage to determine the compliance.

As shown in FIG. 7, the solenoid valve characteristic curve shows the relation between drive voltage and flow rate that changes depending on the pressure value on the cuff side of the solenoid valve.

When the cuff pressure at cuff termination is 200 mmHg and flow rate for accomplishing target deflation rate is 500 ml, solenoid valve drive voltage is determined as 1.45V from the characteristic curve shown in FIG. 7.

The flow rate for accomplishing target deflation rate can be determined as follows based on the compliance detailed above.

$$\text{target flow rate}=K\times\text{target deflation rate}/Cp \quad (9)$$

Constant K includes the proportional relation between pumping amount and voltage and the proportional relation between target deflation rate and flow rate, and the constant can be determined through experiments.

Figure 8:
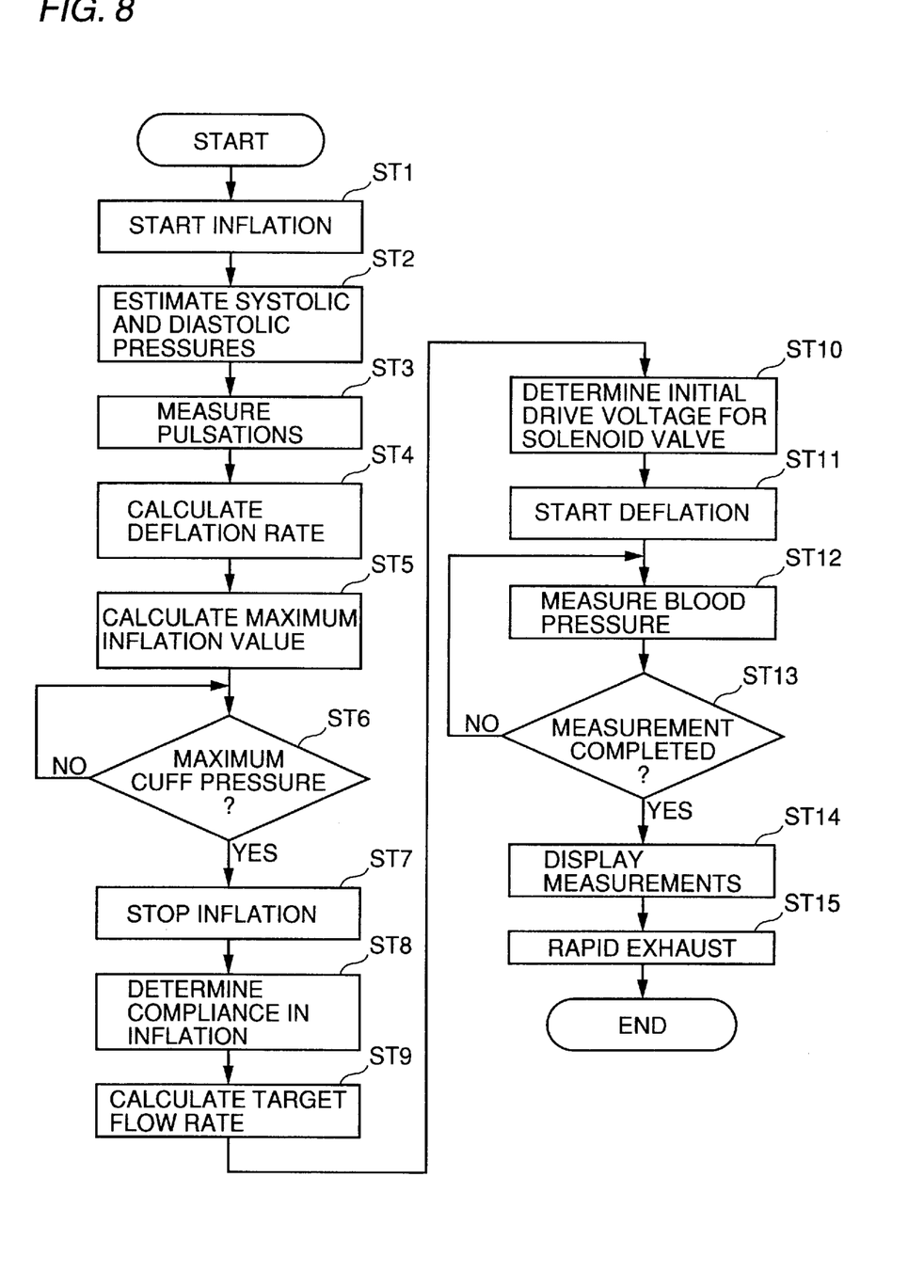
FIG. 8 is a flowchart illustrating an entire operation of the electronic blood pressure meter of the embodiment.

Referring to FIG. 8, an entire operation of the electronic blood pressure meter in measurement is described according to this embodiment.

With power switch 11a turned on, measurement start switch 11b is made on to start a measurement operation. Pressure pump 4 is made on to start inflating cuff 2 (step ST1). After this, with increase of the cuff pressure, the cuff pressure and pulse wave superimposed on the cuff pressure are extracted. Pulse wave feature amount calculating unit 8 obtains pulse wave amplitude data that are some feature amounts of the pulse wave. The cuff pressure and these pulse wave amplitude data in the inflation process are used to estimate approximate systolic and diastolic pressures by blood pressure calculating unit 7 (step ST2), and the number of pulse waves is also measured (step ST3). Here, systolic and diastolic pressures are used as examples of feature amounts.

According to the estimated and measured data, deflation rate determining unit 9 calculates deflation rate def–v by means of formula (1) shown above (step ST4). For example, formula (6) is used to calculate upper limit of inflation value by target inflation value determining unit 11 (step ST5).

The deflation rate and the upper limit inflation value are thus calculated in the inflation process, and then inflation is continued until the cuff pressure reaches the upper limit (step ST6). When the cuff pressure attains the upper limit (step ST6), pressure pump 4 is made off to stop inflation (ST7), compliance is determined from the pressure change and pump drive voltage in inflation (step ST8), a target flow rate is calculated (step ST9), an initial drive voltage of the solenoid valve is determined (step ST10), and accordingly deflation is started (step ST11). Once the deflation process starts, deflation control unit 14 adjusts the deflation to set the deflation rate at the one which has already been calculated in the inflation process.

Deflation is started and then the cuff pressure is detected, pulse wave is extracted and pulse wave amplitude data is extracted as shown in FIG. 3. When a required number of pulse wave amplitude data is gathered, a well-known algorithm is used to determine mean blood pressure, systolic pressure and diastolic pressure and thus blood pressure is determined (measured) (step ST12). Specifically, mean blood pressure is a cuff pressure corresponding to the maximum pulse-wave amplitude, the systolic pressure is a cuff pressure, higher than the mean blood pressure, at a point where the envelope of the pulse wave amplitude and the threshold cross, and the diastolic pressure is a cuff pressure, lower than the mean blood pressure, at a point where the envelop of the pulse wave amplitude and the threshold cross. The algorithm of measuring blood pressure is not particularly limited in this embodiment, and other various methods are applicable.

Measurement of blood pressure is thus completed (step ST13), the measured systolic pressure, diastolic pressure, the number of pulse waves and the like are indicated on display unit 18 (step ST14), solenoid valve 5 is opened to speedily discharge air (step ST15), and thus the operation reaches an end.

Figure 9:
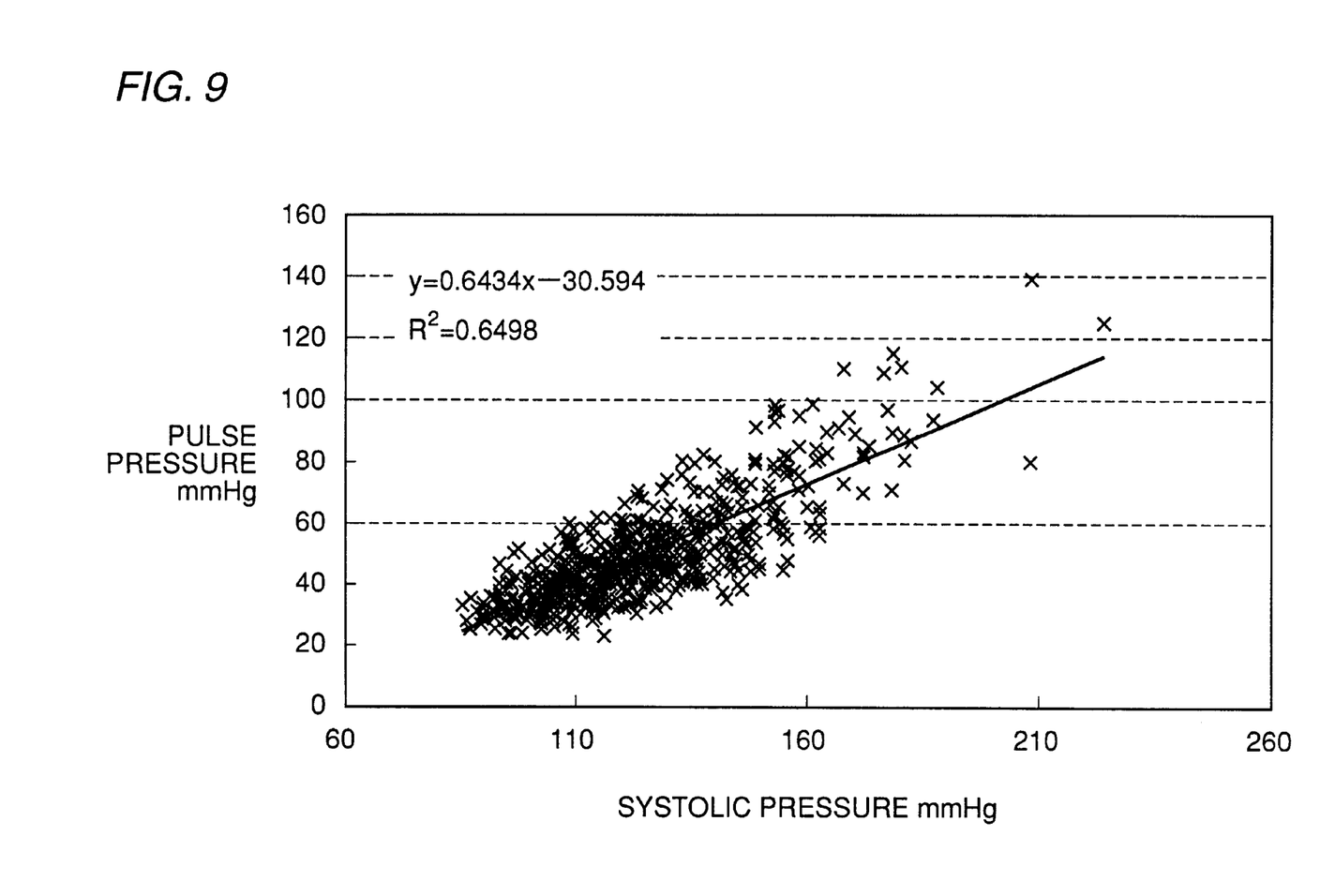
FIG. 9 shows a relation between systolic pressure and pulse pressure, the relation derived from data of actual measurements.

It is noted that inventors have confirmed through actual measurement that the systolic pressure and the pulse pressure are proportional to each other as shown in FIG. 9.

Figure 10:
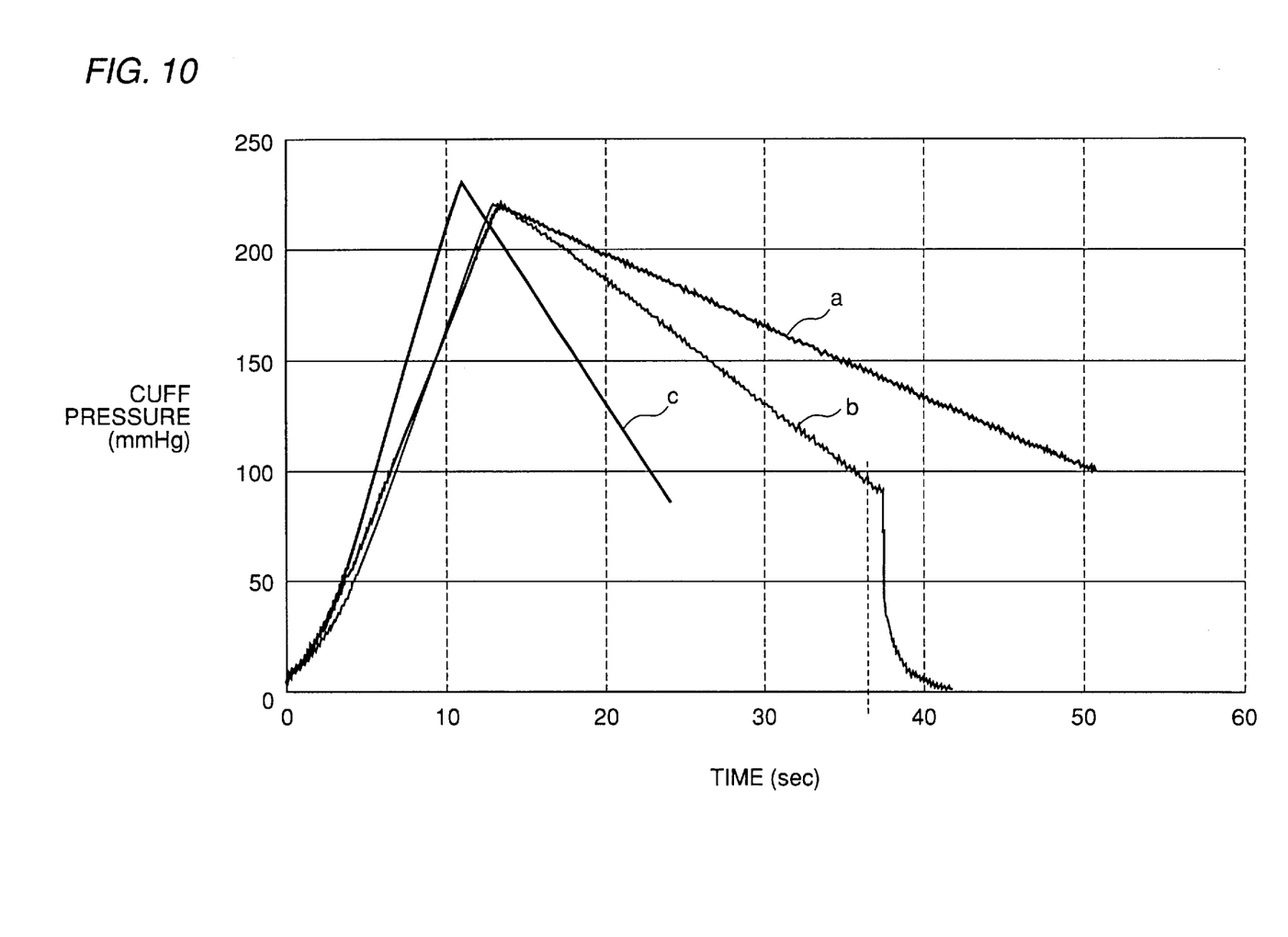
FIG. 10 shows deflation characteristics for comparison between conventional electronic blood pressure meters and the electronic blood pressure meter of the invention.

FIG. 10 shows cuff pressure change characteristics presented for comparison of deflation rate between a common conventional electronic blood pressure meter, a conventional electronic blood pressure meter capable of controlling deflation rate, and the electronic blood pressure meter of this embodiment. Characteristic a represents the one by means of a slow-rate discharge valve of the common conventional electronic blood pressure meter, the deflation rate being 3.19 mmHg/sec. Characteristic b shows the one by the conventional electronic blood pressure meter having the function of controlling deflation rate, and the rate is limited to 5.5 mmHg/sec. Characteristic c represents the electronic blood pressure meter of the present invention. The deflation rate is 11 mmHg/sec. Depending on subjects, such a high deflation rate is applicable to enable a sufficiently high precision of measurement. This deflation rate is twice the conventional one by the electronic blood pressure meter which can control the deflation rate.

As heretofore discussed, according to the invention, deflation rate is calculated according to pulse wave feature amounts that are extracted in a inflation process. An electronic blood pressure meter can thus be provided capable of performing measurement with an optimum deflation rate in a minimum period of time without deteriorating precision.

According to the invention, a target inflation value is determined based on pulse wave feature amounts extracted in the inflation process. An electronic blood pressure meter can thus be provided capable of measuring in a minimum inflation without deteriorating precision.

Further, according to the invention, pressure-rising state, pressure pump drive voltage, pressure at start of deflation and voltage-flow rate characteristics of the solenoid valve are used to determine an initial voltage which enables a flow rate to immediately attain a target deflation rate. Then, the control valve is driven by this voltage and deflation is controlled in a stable manner at a target deflation rate after inflation. An electronic blood pressure meter can accordingly be provided wasting no time before stable control is attained and requiring no excess inflation and thus capable of performing measurement with minimum period of time and pressure without deteriorating precision.

What is claimed is:

1. An electronic blood pressure meter determining blood pressure in a process of gradually depressurizing an artery of at least one area of a human body that has been pressurized to a level higher than systolic pressure, comprising:

pulse wave detecting means for detecting oscillation of a blood vessel wall or pulsating blood flow in the artery occurring in the inflation process;

pulse wave period measuring means calculating, when said pulse wave detecting means detects a plurality of pulse waves, a period between occurrences of respective pulsations;

pulse wave feature amount calculating means receiving as inputs a pulse wave signal of one or a plurality of pulsations supplied from pulse wave detecting means and a representative pressure value synchronizing with pulse wave generation timing supplied from pressure detecting means detecting pressure at the pressurized area of the human body, for extracting a feature amount correlated to at least two of systolic pressure, diastolic pressure and mean blood pressure or correlated to systolic pressure only; and deflation rate calculating means according to an output from said pulse wave feature amount calculating means and the pulse wave period measured by said pulse wave period measuring means for calculating a target deflation rate, characterized in that said deflation rate calculating means uses the feature amount calculated by said pulse wave feature amount calculating means to calculate and determine the target deflation rate to enable detection of a predetermined number of pulse waves between systolic pressure and diastolic pressure in measurement performed in the deflation process.

2. The electronic blood pressure meter according to claim 1, characterized in that the electronic blood pressure meter further comprises target inflation value setting means for determining a target inflation value according to an output from said pulse wave feature amount calculating means.

3. The electronic blood pressure meter according to claim 2, characterized in that said target inflation value setting means determines the target inflation value by adding the calculated target deflation rate to a calculation parameter.

4. The electronic blood pressure meter according to claim 1, characterized in that said pulse wave feature amount calculating means includes blood pressure calculating means for determining at least two of systolic pressure, diastolic pressure and mean blood pressure or only systolic pressure, and target inflation value setting means according to an output of blood pressure value from said blood pressure calculating means for determining said target inflation value.

5. The electronic blood pressure meter according to claim 1, wherein said deflation rate calculating means calculates the target deflation rate based on formula:

$$\text{target deflation rate} = (P_s - P_d - mb) \times P_c / N$$

where $P_s$: pressure correlated to systolic pressure, $P_d$: pressure correlated to diastolic pressure, mb: predetermined offset amount, $P_c$: pulsation period, and N: number of pulsations occurring between systolic pressure and diastolic pressure in deflation.

6. The electronic blood pressure meter according to claim 1, wherein said deflation rate calculating means calculates the target deflation rate based on formula:

$$\text{deflation rate} = (3 \cdot P_s - 3 \cdot P_{max} - mb) \times P_c / N$$

where $P_s$: pressure correlated to systolic pressure, $P_{max}$: pressure correlated to mean pressure, mb: predetermined offset amount, $P_c$: pulsation period, and N: number of pulsations occurring between systolic pressure and diastolic pressure in deflation.

7. The electronic blood pressure meter according to claim 1, wherein said deflation rate calculating means calculates the target deflation rate based on formula:

$$\text{deflation rate} = (3/2 \cdot P_{max} - 3/2 \cdot P_d - mb) \times PC / N$$

where $P_d$: pressure correlated to diastolic pressure, $P_{max}$: pressure correlated to mean pressure, mb: predetermined offset amount, $P_c$: pulsation period, and N: number of pulsations occurring between systolic pressure and diastolic pressure in deflation.

8. The electronic blood pressure meter according to claim 1, wherein said deflation rate calculating means calculates the target deflation rate based on formula:

$$\text{deflation rate} = (a \cdot Ps + b - mb) \times Pc/N$$

where

Ps: pressure correlated to systolic pressure, mb: predetermined offset amount,

Pc: pulsation period,

N: number of pulsations occurring between systolic pressure and diastolic pressure in deflation, and a, b: constants.

9. An electronic blood pressure meter determining blood pressure in a process of gradually depressurizing an artery of at least one area of a human body that has been pressurized to a level higher than systolic pressure, comprising:

pulse wave detecting means for detecting oscillation of a blood vessel wall or pulsating blood flow in the artery occurring in an inflation process;

pressure detecting means detecting pressure at the pressurized area of the human body;

blood pressure calculating means receiving as inputs a pulse wave signal of one or a plurality of pulsations supplied from the pulse wave detecting means and a representative pressure value synchronizing with pulse wave generation timing supplied from the pressure detecting means, for determining at least two of systolic pressure, diastolic pressure and mean blood pressure or systolic pressure only;

deflation rate calculating means according to an output of a blood pressure value from the blood pressure calculating means for calculating a target deflation rate; and pulse wave period measuring means calculating, when said pulse wave detecting means detects a plurality of pulse waves, a period between occurrences of respective pulsations, wherein said deflation rate calculating means receives as inputs said measured pulse wave period and said blood pressure value to calculate deflation rate.

10. The electronic blood pressure meter according to claim 9, characterized in that said deflation rate calculating means uses the blood pressure value calculated by said blood pressure calculating means to calculate and determine the target deflation rate so that a predetermined number of pulse waves are detected between systolic pressure and diastolic pressure in measurement performed in the deflation process.

* * * * *